United States Patent [19]
Sahota et al.

[11] Patent Number: 5,417,653
[45] Date of Patent: May 23, 1995

[54] METHOD FOR MINIMIZING RESTENOSIS

[76] Inventors: Harvinder Sahota, 3861 Wisteria, Seal Beach, Calif. 90740; Nickolai Kipshidze, 9810 Park St., Bellflower, Calif. 90706

[21] Appl. No.: 6,468

[22] Filed: Jan. 21, 1993

[51] Int. Cl.⁶ .............................................. A61N 1/30
[52] U.S. Cl. .................................... 604/20; 606/7; 606/14
[58] Field of Search ............... 604/20, 96; 606/7, 10, 606/21, 13, 14, 23; 607/105

[56] References Cited

U.S. PATENT DOCUMENTS

| | | | |
|---|---|---|---|
| 4,445,892 | 5/1984 | Hussein et al. | 604/101 |
| 4,785,815 | 11/1988 | Cohen . | |
| 4,946,460 | 8/1990 | Merry et al. | 606/21 |
| 5,108,390 | 4/1992 | Potocky | 606/21 |
| 5,109,859 | 5/1992 | Jenkins | 606/7 |
| 5,158,560 | 10/1992 | Sogawa et al. | 606/7 |
| 5,169,395 | 12/1992 | Narcisco, Jr. | 606/7 |
| 5,176,674 | 1/1993 | Hofmann | 606/7 |
| 5,178,616 | 1/1993 | Uemiya et al. | 606/7 |
| 5,269,777 | 12/1993 | Doiron et al. | 606/7 |

FOREIGN PATENT DOCUMENTS

2577410  8/1986  France .

*Primary Examiner*—Jerome L. Kruter
*Attorney, Agent, or Firm*—Knobbe, Martens, Olson & Bear

[57] ABSTRACT

Disclosed is a light angioplasty catheter and method for exposing the interior of a body lumen to a source of light. Light exposure may be accomplished prior to, during, or following conventional balloon dilatation. Also disclosed is a method and apparatus for exposing a preselected portion of vessel wall to a source of light. Relatively low energy light exposure has been found by the inventors herein to both inhibit restenosis following dilatation of a stenotic region, and to inhibit vascular spasms whether or not associated with a stenotic region. It may also arrest progress of a stenosis. Methods are also disclosed for cooling the vascular wall to treat a stenosis. Cooling may be accomplished prior to, during, or following dilatation.

13 Claims, 2 Drawing Sheets

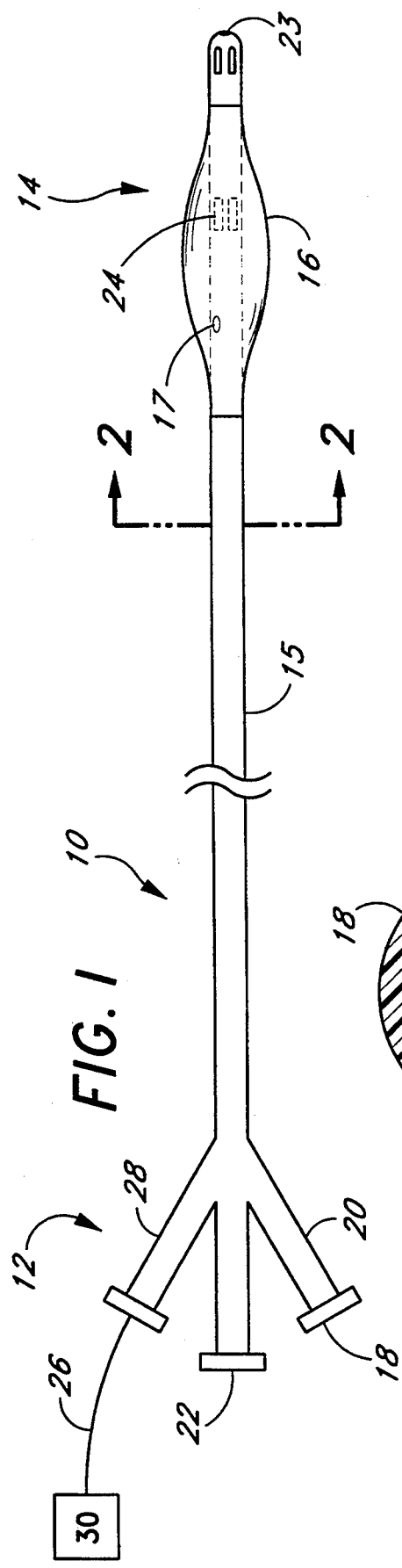
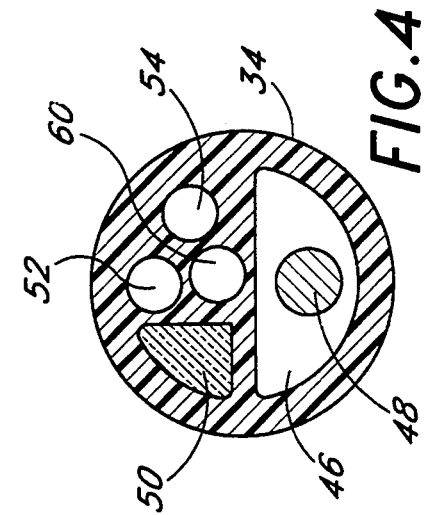
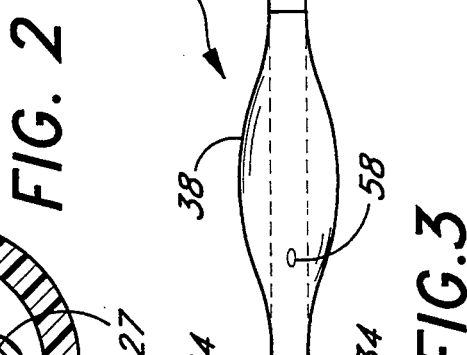
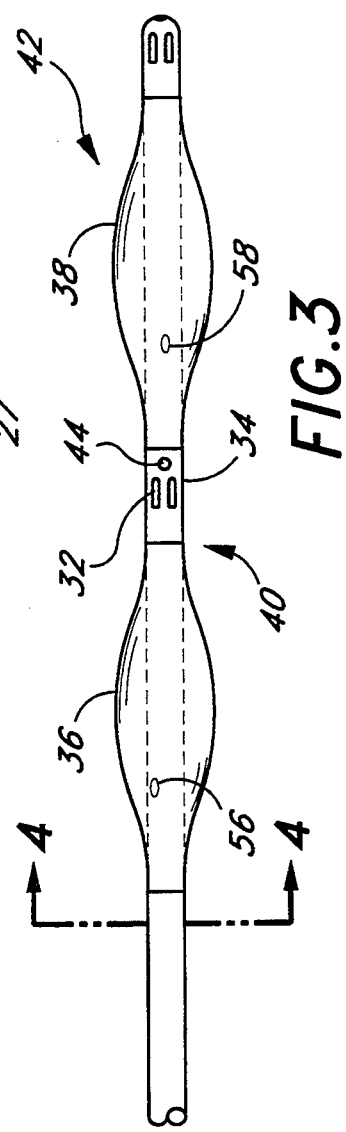

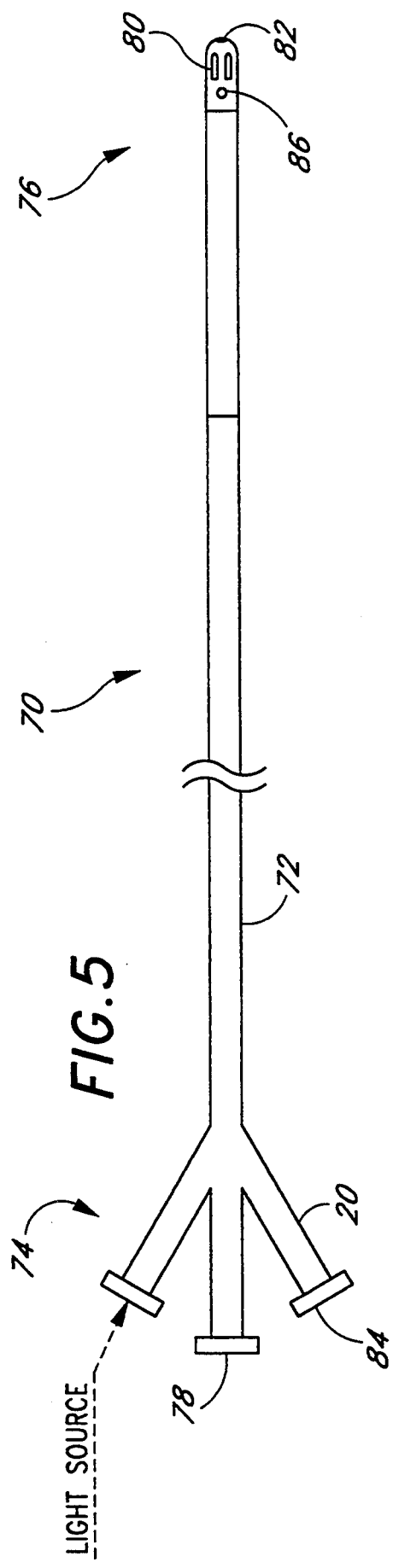

5,417,653

METHOD FOR MINIMIZING RESTENOSIS

BACKGROUND OF THE INVENTION

The present invention relates generally to the field of angioplasty and angioplasty catheters. More specifically, the present invention relates to methods and apparatus for minimizing the occurrence of restenosis following dilatation of a narrowing in a body lumen.

Percutaneous transluminal coronary angioplasty (PTCA), a procedure for treating a patient having a stenosis or constricted region in a coronary artery, has become a widely accepted therapeutic alternative to coronary arterial bypass surgery for many patients. PTCA increases the diameter of the lumen by radial expansion, such as through the use of a dilatation balloon. In the appropriate circumstances, PTCA has a variety of advantages over coronary bypass surgery, including reduction in morbidity, and avoidance of immediate post-operative discomforts and recovery period. Balloon dilatations are also accomplished in a wide variety of other locations in the body to restore patency to an undesirably constricted lumen.

Notwithstanding the advantages of balloon dilatation over more invasive alternatives, balloon dilatation often does not result in a permanent treatment of a stenotic site. Rather, a renarrowing or restenosis of the treatment site is often observed at varying lengths of time following the initial procedure. This is particularly true in the case of PTCA. Patients experiencing a restenosis must thereafter be evaluated for a subsequent medical procedure, such as a further PTCA dilatation or alternative therapy.

Accordingly, there remains a need for a method of minimizing the occurrence of restenosis in a dilated region of body lumen. Optimally, the method would either lengthen time between dilatation procedures, or prevent entirely the need for a subsequent dilatation procedure.

SUMMARY OF THE INVENTION

There is provided in accordance with one aspect of the present invention a catheter for percutaneous transluminal insertion into a body lumen, and exposing a portion of the lumen to light. The catheter comprises an elongate flexible catheter body having proximal and distal ends, and at least one first inflatable balloon on the catheter body, in fluid communication with an elongate inflation lumen extending axially through the catheter body.

At least one light aperture is provided on the catheter body for launching light from the catheter to the wall of the body lumen. The light aperture is in various embodiments disposed proximally of the balloon, distally of the balloon, and within the balloon for propagating light through the inflation media and material of the balloon.

In a further embodiment of the invention, a catheter is provided as above, further comprising a second inflatable balloon. The second balloon is spaced axially apart from the first balloon, and a light aperture is disposed on the catheter body intermediate the two balloons. Preferably, an infusion port is provided on the catheter body intermediate the two balloons, for infusing a media with or without medication which is transparent to the wavelength of light launched from the light aperture.

In accordance with a further aspect of the catheter of the present invention, there is provided an elongate catheter body having at least one light aperture thereon. An infusion port is provided on the catheter body, for infusing a transparent media in the area of the light aperture.

In accordance with a further aspect of the present invention, there is provided a method of inhibiting restenosis in a body lumen following dilatation thereof. The method comprises the steps of selecting a site within a body lumen having a previously dilated stenosis, and exposing the site to a restenosis inhibiting amount of light energy.

In a modification of the method of the present invention, there is provided a method of percutaneous transluminal coronary angioplasty and inhibiting restenosis following dilatation. This method comprises the steps of inserting a balloon dilation catheter into an artery, said catheter of the type having an inflatable balloon and a light aperture thereon. The balloon is positioned within a stenotic region, and inflated to dilate the stenotic region. Either prior to dilation, during dilation or following dilation, the dilated region is exposed to a source of light sufficient to induce a restenosis inhibiting effect.

In accordance with a further aspect of the present invention, there is provided a method of inhibiting arterial spasms. The method comprises identifying the site of an arterial spasm, and introducing a catheter having a light aperture thereon into the artery. The light aperture is positioned within light propagating range of the site, and light is propagated from the catheter to the site to induce a spasm inhibiting effect.

Further aspects and features of the present invention will become apparent from the detailed description of preferred embodiments which follows, when considered together with the attached drawings and claims.

BRIEF DESCRIPTION OF THE DRAWINGS

FIG. 1 is a side elevational view of a dilatation light catheter in accordance with one embodiment of the present invention.

FIG. 2 is a cross-sectional view of the catheter of FIG. 1, taken along the lines 2—2.

FIG. 3 is a side elevational view of the distal portion of a two balloon embodiment of the light catheter of the present invention.

FIG. 4 is a cross-sectional view of the catheter of FIG. 3, taken along the lines 4—4.

FIG. 5 is a side elevational view of a light catheter in accordance with a further embodiment of the present invention.

DETAILED DESCRIPTION OF PREFERRED EMBODIMENTS

The present invention provides methods and apparatus for the post-dilatation treatment of a preselected site in a body lumen, to minimize the occurrence of restenosis following dilatation. Although the present invention will be discussed primarily in the context of a post-balloon dilatation angioplasty procedure, it is to be understood that the methodology and apparatus disclosed herein are of broader applicability.

For example, the efficacy of the present invention is not limited to the coronary artery. Instead, the present invention may be utilized in a post-dilatation treatment in any of a wide variety of cardiovascular or other body lumen. In addition, the methods and apparatus of the present invention are applicable to minimize restenosis following dilatation by means other than conventional balloon angioplasty.

A further aspect of the present invention is directed to inhibition of vascular spasms. This method and apparatus may be applicable both in the context of a dilatation procedure, and to treat spasm of other etiology as will be apparent to one of skill in the art.

Referring to FIG. 1, there is disclosed an elongate dilatation catheter 10 having a proximal control end 12 and a distal dilatation end 14. Dilatation catheter 10 generally comprises an elongate tubular body 15 which may be constructed in accordance with any of a variety of techniques well known in the art. Typically, body 15 comprises an elongate coiled body or extruded plastic, having an appropriate length and diameter for the particular desired application. Catheters intended for use in PTCA will typically have a length on the order of about 170 cm, and a maximum outside diameter of about 1 to 3 French. However, other dimensions may be appropriate for particular applications, as will be understood by one of skill in the art.

The distal end 14 of catheter 10 is provided with an inflatable balloon 16. Balloon 16 generally comprises an inelastic polymeric material such as polyethylene terephthalate, which consistently inflates to a preselected exterior configuration and diameter. Dilatation balloon 16 is in fluid communication with a source of pressurized fluid, by way of port 17 and an elongate lumen 18 which extends proximally through body 15 and is in communication with an inflation port 20 on the proximal end 12 of catheter 10. In the illustrated embodiment, the inflation fluid is preferably transparent to the wavelength of light launched form light aperture 24, as will be discussed.

In an over-the-wire embodiment, the proximal end 12 of catheter 10 is additionally provided with a guidewire port 22. Guidewire port 22 permits access to an elongate central lumen 25 for accommodating a conventional guidewire 27. (See FIG. 2) Lumen 25 extends throughout the length of body 15, and out the distal tip 23 of the catheter. This permits threading the catheter 10 onto the proximal end of a prepositioned guidewire, and advancing the catheter along the guidewire as is well known in the art. Alternatively, the present invention is applicable to monorail or other balloon dilatation catheter configurations.

In one embodiment of the present invention, one or more light apertures 24 are provided on the catheter 10. "Light aperture" in the context of the present invention shall designate that structure on or associated with the catheter 10 which permits light to escape and propagate towards the luminal wall. This includes, for example, light bulbs, light emitting elements, mirrors, openings, distal ends of waveguide or fibers, or other means for releasing light within the lumen. The light aperture can be a dedicated orifice, as illustrated in FIG. 1. Alternatively, it can be a multifunctional orifice such as when fiber optics are advanced down a guidewire lumen or other working channel of a catheter.

In the embodiment illustrated in FIG. 1, light aperture 24 exposes a distal end of one or more fiber optics 26 which extend throughout the length of catheter 10. Fiber optics 26 extend through the proximal end of the catheter such as through an auxiliary port 28, for connection to a suitable light source 30.

The catheter 10 incorporating the present invention can, as desired, include any of a wide variety of additional features or structures known in the art. For example, additional proximal ports can be included in communication with axially extending lumen, such as for aspiration, infusion of medications or other fluids, or infusion of radiopaque dyes to assist in visualization. Steering mechanisms, multiple balloons or other modifications known in the art can readily be incorporated into the catheter of the present invention.

In a drug delivery embodiment, one or more balloons is provided with a plurality of holes for expressing drug within the artery. In another embodiment, medication is expressed through a port on the catheter body, located in between a proximal and distal balloon. The catheters of the present invention are also useful for light activation of drugs or other chemical or biochemical agents which have been rendered inactive through linkage with a photochemically labile bond. Light exposure severs the bond, and releases the active compound as is known in the art.

The light apertures 24 may be provided in any of a variety of configurations depending upon the intended application of the catheter. A single light aperture 24 may be provided, or, preferably, more than one light aperture 24 is provided to produce a greater area of light exposure during operation of the catheter.

Thus, in the illustrated embodiment, two or more light apertures 24 are illustrated as positioned approximately in a plane extending at a perpendicular to the longitudinal axis of catheter 10. Preferably, three or four apertures are spaced equidistant about the periphery of the catheter. Alternatively, a cylindrical or other tubular segment of the catheter body comprises a transparent material to provide a circumferential "window" for exposing one or more light sources.

These configurations produce an arc of light around the interior circumference of the body lumen. Light may only need to be directed to one side of the body lumen, for example, for treatment of an eccentric lesion. However, providing light exposure in a complete 360° ring around the catheter is advantageous due to the difficulty in precise rotational alignment of the distal end of the catheter 10.

Alternatively, two or more light apertures 24 can be spaced apart along the longitudinal axis of the catheter to provide a greater axial length of light exposure. This may be desirable, for example, for the purpose of treating longer lesions. The waveguide in a further embodiment extends axially throughout the length of the catheter and propagates light out the distal tip 23 thereof. The precise number and configuration of light apertures 24 along the catheter body or at its end can be varied considerably, depending upon the light source and intended application, as will be well understood by one of ordinary skill in the art.

In the embodiment illustrated in FIG. 1, light aperture 24 comprises the distal end of a fiber optic 26, for propagating light from a proximal light source 30 to the distal end of the catheter. For this purpose, each light aperture 24 preferably comprises the termination of one or more individual waveguide fibers, for directing light at the luminal wall.

Alternatively, the light source can be positioned within the distal end of the catheter, for direct propagation of light to the luminal wall. For example, any of a variety of light generating structures such as light bulbs, light generating filaments, light emitting diodes, and others well known in the art can be utilized. Wiring for activating distally positioned lights extends proximally through the waveguide lumen. Self contained chemical or biochemical light generating cells having a predetermined exposure duration can also be readily incorporated into the catheter of the present invention. The selection of a particular light source will depend upon the maximum diameter requirements for an intended application, as well as upon energy and wavelength requirements.

In general, the energy of the light delivered out of the distal end of the catheter may be anywhere within a relatively wide, low energy range. The optimal energy is a function of a variety of factors, such as the length of time that the catheter will be tolerated in the lumen, the length of time of light exposure is desired, and the energy thresholds for achieving the beneficial results of the present invention.

In general, a sufficient amount of energy must be transmitted to achieve the functional result of the present invention, yet not produce extensive thermal necrosis to the vascular wall. It has been determined that energy outputs within the range of from about 5 milliwatts to about 100 milliwatts or greater has been satisfactory in in vitro experimentation. Much higher energies in long exposure times will heat the tissue to the point of protein denaturation, which is a result of some laser angioplasty procedures but is not desired in the context of the present invention. Preferably, between about 5 milliwatts and 50 milliwatts are used.

Exposure length is also related to energy level of the light output. In general, exposures in the range of from about 1 second to about 15 to 20 minutes or longer have been utilized. For a particular wavelength and energy level, optimum exposure time can be determined through routine experimentation by one of skill in the art in view of the disclosure herein. In the longer exposures, accommodation is preferably made to ensure perfusion during the treatment. Thus, the present light angioplasty invention is preferably incorporated into a perfusion catheter such as that disclosed in U.S. Pat. No. 4,581,017, the disclosure of which is incorporated by reference herein.

Any of a wide variety of wavelengths of light are believed to be useful for the purposes of the present invention. Selection of a particular wavelengths is a matter which can be accomplished through routine experimentation by one of ordinary skill in the art, in view of the disclosure herein. In particular, factors influencing a selection of wavelength include energy content at the subject wavelength, absorption by the target, and absorption by media between the light source and the target, such as the material of the balloon or other covering over the light source, the inflation media, and hemoglobin or other components in blood which may reside between the light aperture and the vessel wall.

In the embodiment of FIG. 1, where the light is not required to propagate through blood, the inventors prefer visible light in approximately the red light region. In this embodiment, the light aperture 24 is positioned within the balloon 16. This design simplifies the procedure and certain design parameters as will be discussed.

In accordance with the method of the present invention, the light angioplasty catheter illustrated in FIG. 1 is positioned such that balloon 16 is within a stenotic region in a manner well known in the art. Thereafter, the balloon 16 is inflated in a conventional manner to dilate the stenotic region. In this embodiment, inflation media and balloon material will be selected to ensure optimal light transmission properties in the visible range, as will be appreciated by one of skill in the art.

When the balloon 16 is inflated against the arterial wall, most or all of the blood is compressed proximally or distally, so that visible light will propagate readily through the inflation media, and through the material of the balloon directly to the vessel wall.

In this manner, the light treatment can be accomplished simultaneously with balloon dilatation. This procedure can minimize total indwelling time by overlapping the light exposure time with the dilatation time. Alternatively, following balloon dilatation, pressure in the balloon can be maintained or reduced to a non-dilatation mode, yet remain sufficient to hold the exterior of the balloon against the lumenal wall. At that time, the light can be activated to accomplish a post-dilatation light exposure. If accomplished in the coronary or other interruption sensitive artery, perfusion is preferably permitted during one or both of the dilatation and light exposure steps.

In accordance with another embodiment of the present invention, the light aperture is positioned along the axial length of the catheter at a point proximal or distal to the balloon. This embodiment can be accomplished in a single balloon or multiple balloon catheter design.

For example, referring to FIG. 3, one or more light apertures 32 are positioned on the catheter body 34 between a proximal balloon 36 and distal balloon 38. If light is selected which is absorbed by blood, steps must be taken to evacuate the arterial region 40 between proximal balloon 36 and distal balloon 38. For this purpose, catheter 42 is preferably provided with at least one infusion conduit 60 to place an infusion port 44 in fluid communication with a source of infusate.

Referring to FIG. 4, certain functional requirements of the catheter design of FIG. 3 will be more readily observed. Catheter 34 is provided with an elongate guidewire lumen 46 to axially movably accept guidewire 48 such as in a conventional over the wire design. Light lumen 50 is provided for accommodating plurality of fiber optics (not illustrated) in embodiments using a proximally located light source. Proximal balloon inflation conduit 52 and distal balloon inflation conduit 54 are preferably provided to permit selective inflation and deflation of balloons 36 and 38 by ways of ports 56 and 58 respectively. At least one infusion lumen 60 is provided in fluid communication with infusion port 44 for infusing a transparent media to displace blood from arterial region 40.

Set up of the balloon catheter 42 is accomplished, for example, by positioning the light aperture 32 adjacent the treatment site. Either the proximal balloon 36 or the distal balloon 38 is thereafter inflated to hold the catheter in place and occlude blood flow. A clear infusate, such as N-saline or others well known in the art, is then infused into the artery by way of infusion port 44, to displace the blood from arterial region 40 between balloons 36 and 38, and leave a media which is transparent to visible light.

Once a sufficient clearing of the localized portion of the vessel has been accomplished, the second balloon can then be inflated to isolate the treatment area during the light exposure step. Light is thereafter propagated from aperture 32 to the vessel wall.

Preferably, perfusion is permitted through a perfusion lumen in catheter body 34 during the exposure step. A variety of other techniques will be readily envisioned by one of ordinary skill in the art in view of the disclosure herein, for permitting propagation of light from a catheter to a pre-selected treatment sight.

Although not willing to be bound to a particular theory concerning the mechanism of operation, the present inventors believe that exposure to light or other radiation energy kills or deactivates certain smooth muscle cells within the intermediate muscle (mesothelium) layer of the vessel wall. Deactivation of mesothelium cells is believed to inhibit certain restenosis following conventional balloon angioplasty dilatation. In addition, it has been observed by the present inventors that exposure to light as disclosed herein also has an antispasmodic effect on the luminal wall.

Thus, a further aspect of the present invention, provides a method of minimizing spasms in a vascular wall. This method comprises the steps of positioning a light emitting catheter within a body lumen, and exposing the interior of the body lumen to light to inhibit spasms in the wall. Vascular, and particularly arterial, spasms arise from a variety of etiology, including irritation such as that produced by the presence of a balloon or other catheter. Accordingly, the occurrence of arterial spasms can be intensified by the presence of a treatment catheter within the artery. The application of light to the arterial wall prior to, during and/or following balloon dilatation can therefore have a beneficial anti-spasmodic effect, thereby permitting optimal perfusion at all times.

It has further been determined by the present inventors that the inhibition of arterial spasms is maximized during the period of actual light exposure. However, a residual inhibition remains following interruption of the light exposure.

In accordance with a further aspect of the present invention, there is provided a light emitting catheter for directing light to a preselected site in a body lumen. Referring to FIG. 5, there is disclosed a catheter 70 having an elongate tubular catheter body 72 with a proximal end 74 and a distal end 76. Catheter 70 is preferably provided with a central guide wire lumen (not illustrated) and guidewire port 78 in an over-the-wire embodiment, or other provisions for steering the catheter 70 as are known in the art.

Catheter 70 is provided with at least one light aperture 80 thereon for permitting exposure of a portion of vessel wall to a source of light. Light aperture 80 may be positioned at the distal end 82 of the catheter or along the lateral surface thereof, as has been described in connection with previous dilatation catheter embodiments herein. Light aperture 80 permits propagation of light from either a distal light source located within the catheter or a proximally located light source coupled with a fiber optic or other waveguide, as has been previously discussed.

In accordance with the arterial spasm inhibition aspect of the present invention, the light catheter 70 is transluminally advanced and positioned so that the light aperture 80 is in the area to be treated. Light is propagated towards the vessel wall to accomplish a spasm inhibiting result. In an embodiment utilizing light which is strongly absorbed by hemoglobin, and in which the light catheter is not snugly fitted against the wall to be treated, an infusate which is relatively transparent to the wavelength of light selected is preferably conducted into an infusion port 84, through an infusion lumen in the light catheter and introduced into the vessel via one or more ports 86 in the region of the light aperture 80. Light initiated spasm inhibition may be desirably performed prior to, during or following a balloon dilatation of the vessel. Alternatively, it can be used to treat spasms of other etiology, unrelated to arterial stenosis or the dilatation procedure.

The light emitting catheter of the present invention may also be utilized to inhibit restenosis following dilatation utilizing conventional balloon dilatation catheter techniques. In accordance with this aspect of the present method, a balloon angioplasty or other dilatation of a body lumen is conducted using techniques now conventional in the art. Following deflation and removal of the balloon, the light catheter of the present invention is advanced through the luminal system and positioned with the aperture 80 in the region of the vessel wall to be treated. The light source is activated, in accordance with the time and energy parameters discussed supra, to accomplish an inhibition of restenosis. After the appropriate time, the light is deactivated and/or the catheter is withdrawn.

It has also been observed by the present inventors that both the incidence of restenosis and vascular spasm is reduced during and following cooling of the vascular wall at a treatment site. In addition, cooling the vascular wall, may arrest the progress of a developing stenosis.

Thus, in accordance with a further aspect of the present invention, there is provided a method of inhibiting restenosis or vascular spasm comprising the steps of selecting a treatment site in a vascular lumen, and reducing the temperature of at least a portion of the tissue at the treatment site. Temperature reduction is preferably accomplished by infusion of a refrigerated coolant, such as n-saline or other infusate known in the art. The refrigerated infusate is optionally charged with one or more medications which may desirably be administered at the treatment site. The method may also be used to treat a stenosis to arrest further restriction, as will be discussed.

It has been determined that refrigerated coolants in the temperature range of from about 0° C. to about 10° C. exhibit a suitable cooling effect. Media which has been refrigerated to a slightly warmer temperature may also produce a desirable effect, depending upon the total heat content removed from a given portion of the vessel wall by the infused volume of coolant. As will become apparent to one of skill in the art, relatively warmer coolants will require a relatively larger fluid volume to remove a given quantity of heat from a localized region of vessel wall. Such fluid volume may or may not be desirable depending upon the circumstances of the patient.

Introduction of the coolant can be accomplished in any of a variety of manners, as will be appreciated by one of skill in the art. Preferably, the coolant is introduced by way of a porous infusion balloon, as has been previously described. The number and diameter of pores extending through the delivery balloon can be optimized through routine experimentation by one of skill in the art. Alternatively, coolant may be delivered by way of a fluid delivery port on a catheter, such as delivery port 86 (FIG. 5).

Alternatively, the balloon in a standard balloon dilatation procedure can be inflated with cooled or supercooled inflation fluid. In this manner, the tissue of the vessel wall which is in contact with the dilated balloon will be cooled simultaneously as it is dilated.

The temperature reduction treatment may be accompanied by one or more of the light exposure treatment and drug delivery treatment described herein. For example, the infusate utilized in previous embodiments to displace blood and permit propagation of light from a light aperture to the vessel wall may be reduced to the desired refrigerated temperature prior to introduction. In this manner, the vessel wall will be simultaneously cooled and exposed to a light source. Alternatively, a light source within a balloon can be activated while the balloon is inflated with a refrigerated coolant.

It is believed by the present inventors that reducing the temperature of the infusate or the balloon inflation fluid to the area of from about 0° C. to about 10° C. will help reduce the inflammation in the artery wall, which has been caused or aggravated by the presence of the balloon dilatation or other treatment catheter. It is believed to also numb the proliferating smooth muscle in the artery, which is at least partially responsible for restenosis. Thus, any of the application of light, cooling and drugs, as well as combinations of these three modalities, are believed to be efficacious for at least temporarily arresting or inhibiting the progress of a stenosis. In addition, optimal combinations of two or more modalities in the same treatment can be readily determined through routine experimentation by one of ordinary skill in the art in view of the disclosure herein.

The foregoing methodology is additionally believed useful for a prophylactic treatment of arterial stenosis. In general, balloon dilatation is not indicated for a stenosis until 60% or 70% or a higher occlusion is found to exist. Lesser occlusions are often not yet clinically dangerous, although they may be progressively increasing over time. Using the methodology and apparatus of the present invention, a 50% occlusion or lower can be advantageously treated by cooling, light or drug exposure to inhibit further restriction of the artery to a clinically significant stage.

In one application of the preventative therapy in accordance with the present invention, a primary lesion is selected within an artery for balloon dilatation. Following conventional dilatation and application of methods disclosed previously herein, a secondary lesion in the same patient which may not yet warrant balloon dilatation is selected. The secondary lesion is exposed to a source of light, such as through the use of the catheters disclosed herein, either alone or in combination with a cooling of the vessel wall. Alternatively, the lesion is cooled without the application of light. In this manner, the progress of the secondary lesion may be inhibited or halted so that either no progression to a greater restriction will occur, or the ultimate balloon dilatation procedure will be effectively delayed.

The restenosis inhibition and arterial spasm inhibition effects of the present invention will be further understood by reference to the following examples.

Experiment 1

Effect of Visible Light on Mesothelium

Experiments were conducted to determine the effect of exposure of smooth muscle cell to light. Smooth muscle cell cultures from animal arteries were raised in accordance with conventional techniques. An aliquot of smooth muscle cell culture was placed into each of a series of test tubes. A first set of test tubes was exposed to ambient laboratory room overhead light (control group). A second set of test tubes was divided into subgroups, and each was exposed to red light at varying energies within the 5-15 milliwatt range. Exposure was continuous wave, and for a period of from about 5 seconds to one hour.

Following exposure, both the control and experimental sets of cells were examined under the microscope and electron microscope. Histology revealed no change to the cells exposed to ambient room light. However, cells exposed to red light exhibited changes suggestive of destruction, including observed vacuolization, destruction of the nucleus, cytoplasm and cytoplasmic structures.

Experiment 2

Effect of Light Exposure on Animal Arteries

Samples of rabbit arteries having outside diameters of approximately 4 mm were obtained. Electron microscope examination revealed relatively smooth arterial walls. A portion of the arteries were thereafter exposed to red laser light of approximately 15 milliwatts for 20 to 30 minutes. Subsequent examination under the electron microscope revealed pockets within the arterial wall where the cellular material had been destroyed.

Although the present invention has been described in terms of certain preferred embodiments and methods, other embodiments of the structure and methods will be apparent to one of ordinary skill in the art from the disclosure herein. Accordingly, the present invention is not limited to the specific embodiments herein, but rather is intended to encompass all of the embodiments and methodology within the scope of the claims appended hereto.

We claim:

1. A non-ablative method of inhibiting restenosis in a body lumen following dilatation of a stenosis, comprising:
    selecting a body site within a lumen having a previously dilated stenosis;
    inserting a catheter into said lumen, said catheter of the type having a light aperture positioned proximally from a distal tip of said catheter; and
    laterally launching a restenosis inhibiting amount of light energy from said aperture to said body site to expose substantially the circumference of the body lumen at said body site to the light energy, wherein said light energy is below an energy level sufficient to produce thermal protein denaturation in the vascular wall after exposure to the light energy for more than a second.

2. The method of claim 1, wherein the catheter is a balloon dilatation catheter having an inflatable balloon with the light aperture positioned within the balloon, and wherein said step of inserting comprises positioning the inflatable balloon within a stenotic region, said method further comprising the steps of:
    inflating the balloon; and
    while the balloon is inflated, launching the restenosis inhibiting amount of light energy through the inflation media and through the balloon wall to expose the dilated region to the light energy.

3. A method as in claim 2, wherein at least a portion of said exposing step is accomplished prior to said inflation step.

4. A method as in claim 2, wherein at least a portion of said exposing step is accomplished simultaneously with said inflation step.

5. A method as in claim 2, wherein at least a portion of said exposing step is accomplished following said inflation step.

6. The method as in claim 1, wherein the light is in the visible red range.

7. The method of claim 1, further comprising the steps of:

exposing at least a portion of the dilated region to a refrigerated fluid to treat the dilated region to inhibit restenosis without significant ablation resulting from exposure to the refrigerated fluid.

8. A method as in claim 7, wherein said fluid is refrigerated to a temperature of no more than about 15° C.

9. A method as in claim 7, wherein said fluid is refrigerated to a temperature of no more than about 10° C.

10. A method of inhibiting arterial spasm, comprising the steps of:

identifying the site of an arterial spasm;

introducing a catheter having a light aperture thereon into the artery;

positioning the light aperture within light propagating range of said site; and propagating light from the catheter to said site.

11. A method as in claim 10, wherein said light comprises visible light.

12. A method as in claim 11, wherein said light has an energy within the range of from about 5 milliwatts to about 100 milliwatts.

13. A method as in claim 10, wherein said light exposure time is more than about 1 second.

* * * * *